United States Patent [19]

Kauphusman et al.

[11] Patent Number: 4,846,171
[45] Date of Patent: Jul. 11, 1989

[54] LASER CATHETER ADJUSTABLE CONTROL APPARATUS

[75] Inventors: James V. Kauphusman, Champlin; Bruce H. Neilson, Brooklyn Park, both of Minn.

[73] Assignee: GV Medical, Inc., Minneapolis, Minn.

[21] Appl. No.: 194,142

[22] Filed: May 16, 1988

Related U.S. Application Data

[63] Continuation of Ser. No. 915,507, Oct. 6, 1986, abandoned.

[51] Int. Cl.$^4$ ............................................. A61B 17/36
[52] U.S. Cl. ................................ 128/303.1; 128/395; 128/398; 219/121.6; 219/121.61
[58] Field of Search .......... 128/303.1, 303.13–303.15, 128/395–398, 6–8, 344, 656, 658; 219/121.6, 121.61; 200/60, 321, 322, 327, 328, 291

[56] References Cited

U.S. PATENT DOCUMENTS

| | | | |
|---|---|---|---|
| 3,720,896 | 3/1973 | Beierlein | 128/303.13 |
| 4,025,743 | 5/1977 | Oswald | 200/60 |
| 4,097,703 | 6/1978 | Houser | 200/321 |
| 4,097,705 | 6/1978 | Harvell | 200/321 |
| 4,669,465 | 6/1987 | Moore et al. | 128/303.1 |

Primary Examiner—Ruth S. Smith
Attorney, Agent, or Firm—Orrin M. Haugen; Thomas J. Nikolai; Frederick W. Niebuhr

[57] ABSTRACT

An apparatus is disclosed for advancing an optical fiber in a laser enhanced transluminal angioplasty catheter, and for controlling the introduction of laser energy into the fiber. The device includes a catheter and a fiber advance housing. The optical fiber runs through the catheter and housing, and is optically connected to a source of laser energy. A fiber advance assembly, mounted in the housing, reciprocates to advance and retract the fiber relative to the catheter and housing. An actuator member is provided inside the housing to slide independently of the fiber advance assembly. A switching means, provided in the housing, is closed to enable introduction of laser energy into the optical fiber whenever the fiber advance assembly is disposed forwardly of a select position relative to the actuator member. The switching means is open, thereby preventing introduction of laser energy into the fiber, whenever the fiber advance assembly is disposed rearwardly of the select position. The actuator position is adjustable through a zero adjust slide, connected to the actuator and slidable relative to the housing.

13 Claims, 4 Drawing Sheets

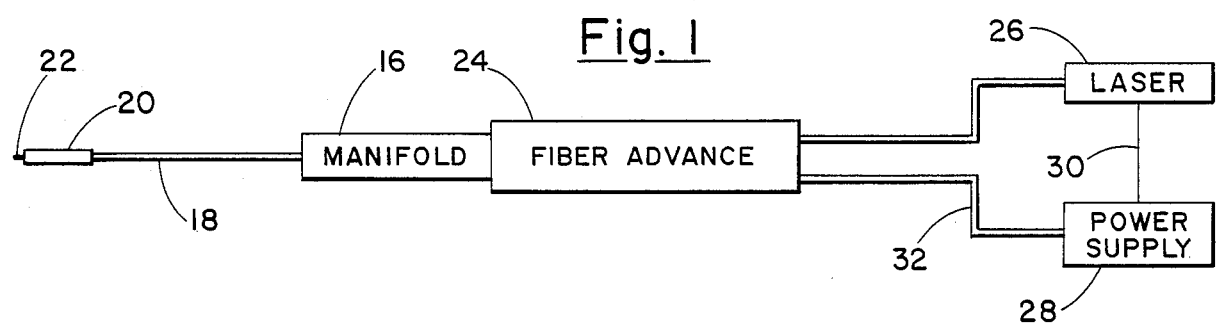
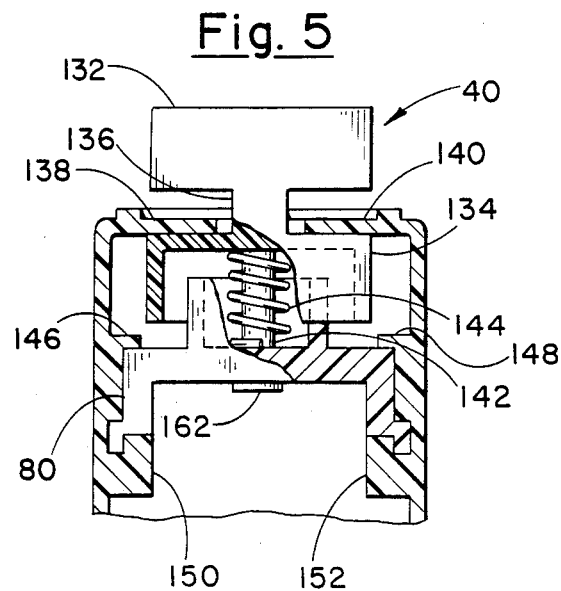
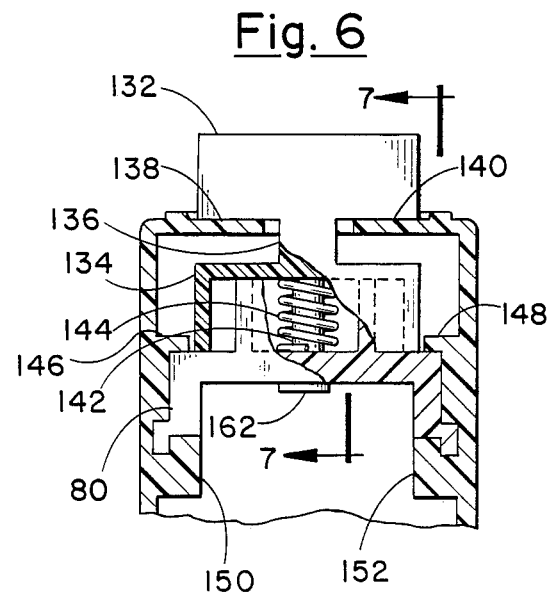
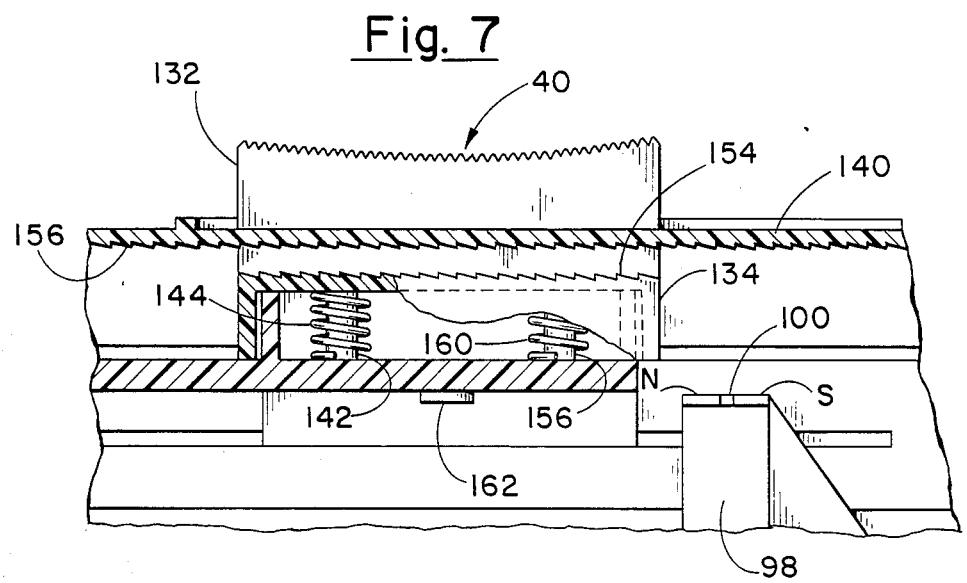

LASER CATHETER ADJUSTABLE CONTROL APPARATUS

This is a continuation of application Ser. No. 915,507, filed Oct. 6, 1986 now abandoned.

BACKGROUND OF THE INVENTION

The present invention relates to laser enhanced transluminal angioplasty catheters and particularly to apparatus in such catheters for inserting an optical fiber into the catheter, and for controlling the times at which laser energy is introduced into the fiber.

Angioplasty catheter devices have been found useful in treating occlusions formed in blood vessels, for example, from plaque build-up. In a laser enhanced catheter, an optical fiber is used to transmit a beam of laser energy from a generator to the fiber distal end, where the laser energy is delivered to and against the obstruction. Under controlled exposure to the laser energy, the obstruction is partially removed, reduced in size, or eliminated entirely, effectively re-opening the blood vessel to restore normal circulation.

The success of this procedure, however, is largely dependent upon the skill with which the physician manipulates the catheter and optical fiber. Typically, fluoroscopy techniques, such as incorporation of radiopaque markers near the catheter distal end, assist in control of the catheter. A problem more particular to the optical fiber is the requirement that it be advanced beyond the catheter distal end by a controlled amount. To avoid damage to the fiber, it is preferably retracted within the catheter while the catheter is inserted, to be later advanced beyond the catheter tip. Care must be taken to avoid introducing laser energy into the fiber until its distal end has emerged beyond the catheter tip. Otherwise, the catheter lumen containing the fiber can be damaged.

U.S. Pat. No. 4,669,465, assigned to the assignee of the present application, discloses a laser catheter control and connecting apparatus including a zero adjust knob 60 threadedly engaged to the fiber advance manifold 14, for adjusting the position at which a Hall effect switch automatically turns off the laser source upon optical fiber retraction. While this apparatus can effectively ensure against premature transmission of laser energy through the optical fiber, it requires the exclusive attention of the physician or other operator, and its adjustment requires both hands.

It therefore is an object of the present invention to provide a conveniently adjustable apparatus for selectively enabling and disabling transmission of laser energy through an optical fiber.

Another object of the invention is to provide a zero positioning switch in a laser enhanced transluminal catheter that can be adjusted with one hand, and without demanding the exclusive attention of the physician or other user.

Yet another object of the invention is to provide a zero positioning switch mounted to a fiber advance housing, and adjustable by an operator using the same hand that is holding the fiber advance housing.

SUMMARY OF THE INVENTION

To achieve these and other objects, there is provided an apparatus for advancing and retracting an energy transmitting fiber within a catheter lumen, and for selectively transmitting energy through the fiber. The apparatus includes a fiber advance housing, a catheter having at least one lumen, and means for securing a proximal end of the catheter integrally with respect to the housing, with the lumen open to the housing. A source for generating energy and an energy transmitting fiber are provided. The fiber is partially contained in the lumen, runs through the housing, and is optically connected to the source. A fiber advance assembly is mounted to reciprocate longitudinally with respect to the housing, and is fixed to the fiber to alternatively advance and retract the fiber relative to the housing and catheter. A distal end portion of the fiber extends beyond the distal end of the catheter when the fiber is fully advanced, but is entirely contained in the lumen when retracted.

The apparatus also includes an actuator member inside the housing and mounted to slide longitudinally with respect to the housing over a limited range, independently of the fiber advance assembly. A moving member travels longitudinally relative to the housing and extends outside of the housing. A linking means joins the moving member to the actuator member whereby the actuator member moves longitudinally with the moving member.

A locking means, provided along the path of travel of the moving member, includes at least one first locking surface on the moving member, a complementary second locking surface integral with the housing and facing each first locking surface, and a biasing means for urging the first and second locking surfaces into engagement with each other. A switching means, provided in the housing, is closed whenever the fiber advance assembly is disposed forwardly of a select position with respect to the actuator member. The switching means is open whenever the fiber advance assembly is disposed rearwardly of the select position.

Preferably, the switching means includes a Hall effect switch comprised of a permanent magnet integral with the fiber advance assembly, and a sensor integral with the actuator member and responsive to its longitudinal position relative to the magnet.

The linking means can include a plurality of pins integral with the moving member, with each pin extended through an associated aperture in the actuator member. A preferred biasing means includes a coil spring surrounding each pin and under compression between the actuator member and the moving member.

The moving member is advantageously positioned to extend upward from the top of the fiber advance housing, with the biasing means urging the moving member upward into its locking engagement. Given this arrangement, the operator can release the moving member simply by pressing it downward with the thumb of the hand gripping the fiber advance housing. Sliding of the moving member is then a matter of moving the thumb forward or backward.

A significant advantage of this structure resides in the fact that the moving member may be adjusted with one hand, and without visual or other undue attention directed to the fiber advance housing. Consequently, the physician's attention can be directed to the angioplasty procedure at hand, and he or she can rapidly adjust the zeroing switch in response to any emergency.

This feature is further enhanced when the first and second locking structures include, respectively, a plurality of transversely directed teeth formed in a first surface of the moving member, and a plurality of complementary teeth formed in a second surface inside of the housing and facing the first surface. By pressing upon the moving member a sufficient amount to permit its movement, yet not completely freeing the teeth from one another, the physician gains a tactile sense of the degree of moving member displacement, further reducing the amount of visual attention required to operate the fiber advance housing.

IN THE DRAWINGS

These and other features and advantages of the invention are more clearly understood upon reading the following detailed description and consideration of the accompanying drawings, in which:

FIG. 1 is a diagrammatic representation of the operation of a laser enhanced transluminal angioplasty catheter;

FIG. 5 is an enlarged sectional view taken along the line 5—5 in FIG. 3 showing a zero adjust slide constructed in accordance with the present invention;

FIG. 6 is a sectional view similar to that in FIG. 5 showing the slide of FIG. 5 disengaged from the housing; and FIG. 7 is a sectional view taken along the line 7—7 in FIG. 6, further including part of a fiber advance slide in side elevation.

DETAILED DESCRIPTION OF THE PREFERRED EMBODIMENT

Figure 2:
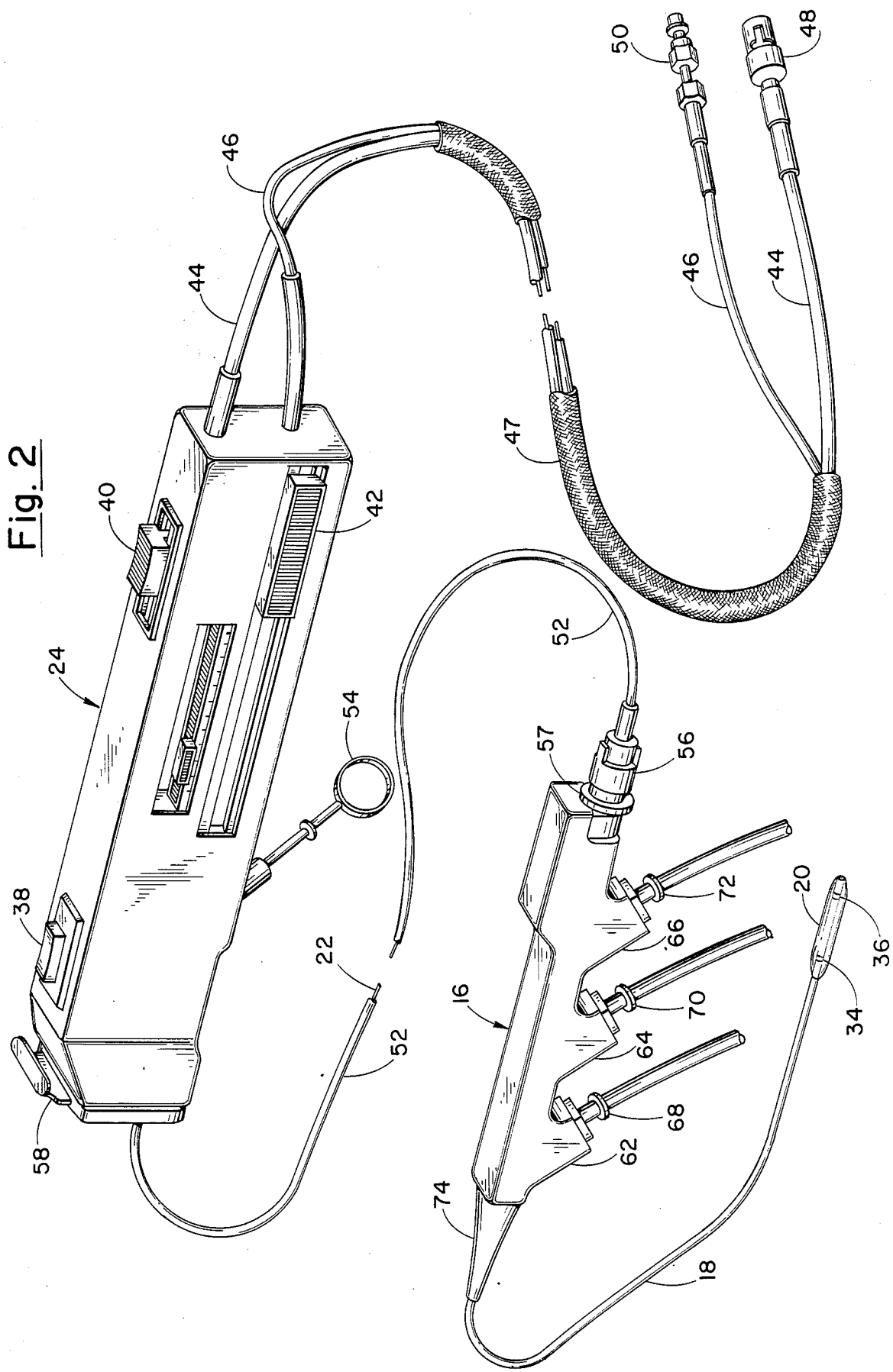
FIG. 2 is a perspective view of a fiber advance housing and catheter manifold constructed in accordance with the present invention.

Turning now to the drawings, there is shown schematically in FIG. 1 an angioplasty catheter assembly including a catheter manifold 16 and an angioplasty catheter 18 extended from the forward end of the catheter manifold. At the distal end of the catheter is a balloon 20.

An optical fiber 22 is contained in catheter 18, with its distal tip shown in an operative position, i.e. extended slightly beyond the distal end of the catheter. The optical fiber runs rearwardly from the catheter through the catheter manifold into a fiber advance housing 24, wherein the optical fiber may be advanced or retracted in the catheter as will be later explained. Optical fiber 22 also extends from housing 24 to a laser source 26 which is actuated by a power supply 28 through a first electrical path 30. Through a second electrical path 32 between fiber advance housing 24 and power supply 28, a control switch in the housing selectively enables power supply 28, and therefore controls the transmission of laser energy through optical fiber 22. If desired, radiopaque markers are provided near the catheter distal end as shown at 34 and 36, to enable a physician to determined the location of the catheter when it is inserted into a blood vessel.

As seen in FIG. 2, fiber advance housing 24 and catheter manifold 16 are separable from one another, which enables a controlled insertion of optical fiber 22 through the manifold and into catheter 18. Provided on the top of housing 24 is a laser actuator switch 38, electrically connected to power supply 28, for enabling the transmission of laser energy through optical fiber 22. Rearwardly of switch 38 is a zero adjust slide 40, which comprises a movable member mounted to slide longitudinally with respect to the housing. Also movable slidably in the housing is a fiber advance member or slide 42.

Extended from the rearward end of fiber advance housing 24 is an electrical cable 44 through which laser actuator switch 38 and zero adjust slide 40 are electrically linked to power supply 28. Adjacent cable 44 is an optical fiber cable 46 which contains a portion of optical fiber 22. A flexible sleeve 47 keeps the cables together. An electrical connector 48 at the proximal end of electric cable 44 is adapted for connection to the power supply, while an optical connector 50 at the proximal end of the optical fiber cable optically links fiber 22 with laser source 26.

Between fiber advance housing 24 and catheter manifold 16 is an optical fiber sheath 52 which enters the forward end of the fiber advance housing and emerges beneath the housing to a pull ring 54. The sheath is connected to a sheath connector 56 shown against a manifold connector 57 at the rearward end of manifold 16. A housing connector latch 58 mounted on the forward end of the fiber advance housing, lockingly engages manifold connector 57 to connect the fiber advance housing to catheter manifold 16 when desired.

The catheter manifold has first, second and third extensions 62, 64 and 66, to which are connected first, second and third luers 68, 70 and 72. First luer 68 provides fluid to balloon 20 in order to control its inflation and deflation. Second and third luers 70 and 72 deliver treatment fluids, as required, to a central lumen in catheter 18. A conical relief member 74 supports the proximal portion of catheter 18 near the manifold forward end, protecting it against sharp bends.

Figure 3:
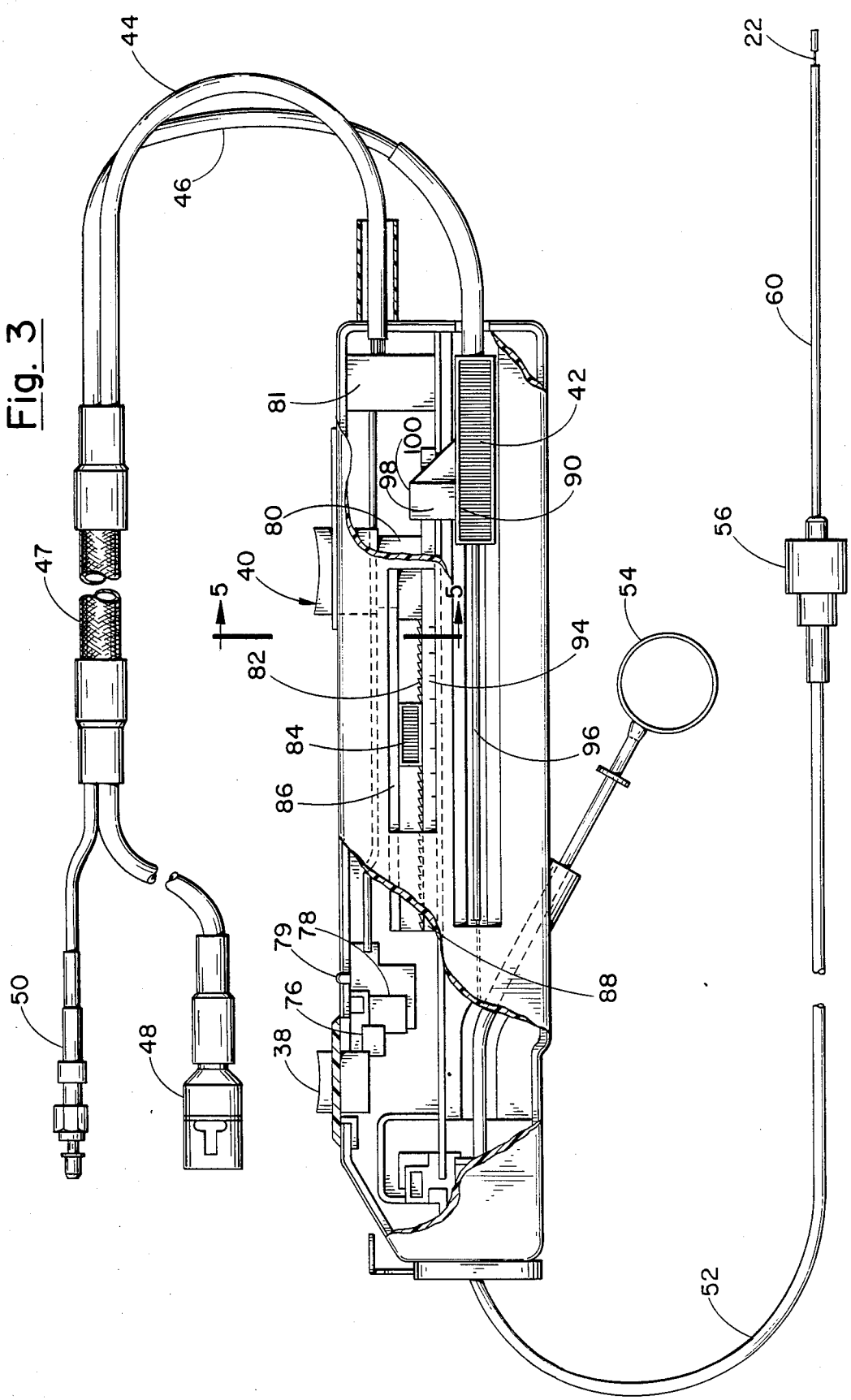
FIG. 3 is a side elevation of the fiber advance housing of FIG. 2, with portions broken away to illustrate certain features.

FIG. 3 shows sheath connector 56 detached from catheter manifold 16, to reveal a tubular fiber guide 60 which aids insertion of optical fiber 22 into the catheter manifold and catheter, as is later explained. A forward portion of the outside wall of fiber advance housing 24 is removed to reveal a first electrical contact 76 integral with laser actuator switch 38, and a second electrical contact 78 integral with the housing. To activate laser source 26, the laser actuator switch is pressed downward and moved backwardly or to the right as viewed in the figure, bringing the electrical contacts together to complete the circuit. Behind switch 38 is a light emitting diode (LED) 79 which, when lit, indicates that laser source 26 can be activated by switch 38. Electrical connections to cable 44 are through a printed circuit card 81 at the rear of the housing.

A rearward portion of the housing wall is removed to reveal that zero adjust slide 40 is connected to move longitudinally with a zero adjust actuator 80, which slides longitudinally with respect to the fiber advance housing along with the zero adjust slide. Integral with actuator 80 are two side-by-side longitudinally directed rows of serrations, one of which is shown at 82. A longitudinal gap between the separate rows accommodates a downwardly depending portion of an adjustable stop 84. Adjustable stop 84 rides along an upper rail 86 formed in fiber advance housing 24, and can slide with respect to the housing along the zero adjust slide 40 and actuator 80. Also, stop 84 can be disengaged from the serrations and moved to alternative longitudinal positions with respect to the actuator. Forwardly of adjustable stop 84 is a bar 88 which spans the gap between the rows of serrations to provide a second stop, fixed with respect to actuator 80.

A fiber advance assembly 90 includes fiber advance slide 42 that slides on a lower, fiber advance rail 94 formed in the housing. A fiber advance tube 96 extends forwardly from the slide. A leg 98 extends upwardly from slide 42, and is positioned to travel in the gap between the adjacent rows of serrations to permit longitudinal advancing and retracting of the assembly. Once it encounters either adjustable stop 84 or bar 88, leg 98 prevents any further forward travel of fiber advance assembly 90. Mounted at the top of leg 98 is a permanent rare earth magnet 100, which cooperates with a sensor mounted in actuator 80 to create a Hall effect switch as is later explained.

Optical fiber 22 runs continuously from optical connector 50 to the distal end of tubular fiber guide 60 and can be considered to include a proximal portion generally contained within optical cable 46, a distal portion contained in sheath 52 and tubular guide 60, and an intermediate portion attached to fiber advance slide 42 and running through fiber advance housing 24.

Figure 4:
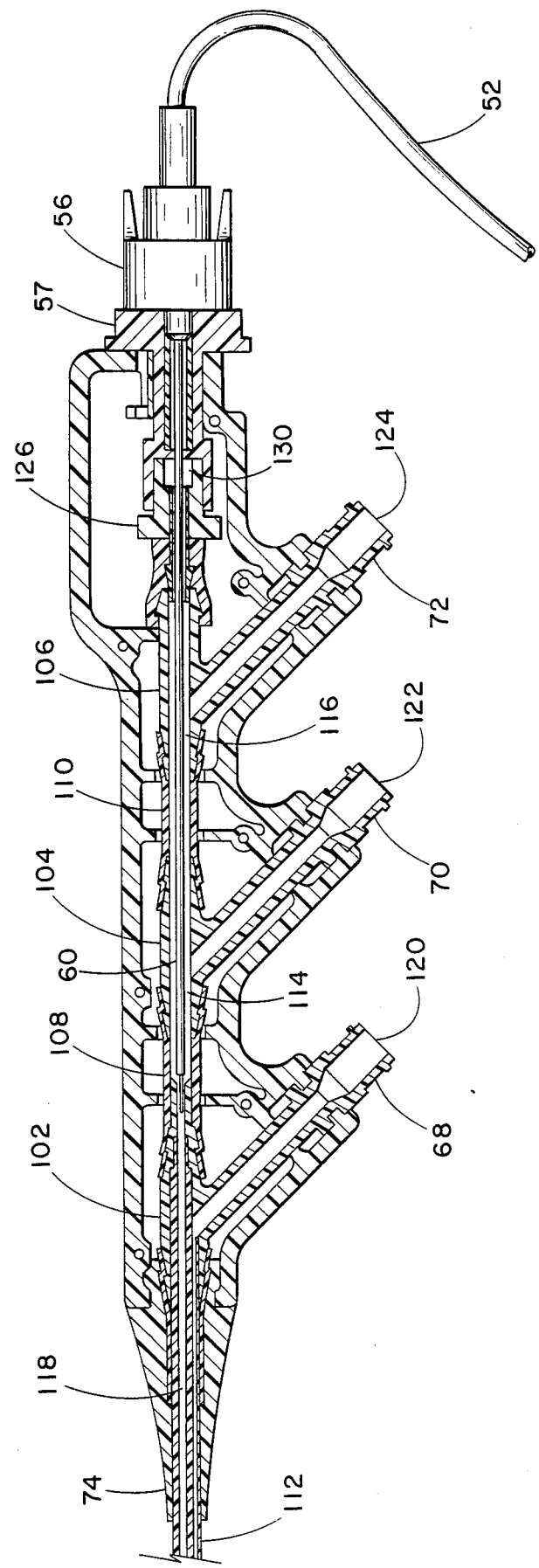
FIG. 4 is a sectional side elevation of the catheter manifold of FIG. 2.

In FIG. 4 it is seen that first, second and third luers 68, 70 and 72 have upper longitudinal portions or luer branch fittings 102, 104 and 106, respectively, joined together by first and second lengths 108 and 110 of a heat shrink tubing. Formed through first upper portion 102 is a central longitudinal passageway having a diameter corresponding to that of a central lumen 112 in catheter 18. Larger longitudinal passageways are provided through second and third upper portions 104 and 106, to form in catheter manifold 16 a single passageway 114 with an enlarged proximal or rearward portion 116, and a smaller distal portion 118, with the diameter reduction occurring along first heat shrink tubing length 108. A first central channel 120 of first luer 68 is open to the distal passageway portion, while second and third channels 122 and 124 of luers 70 and 72, respectively, are open to enlarged portion 116. A seal retaining cap 126 and manifold connector 57 enclose a seal 130, which prevents backflow of fluids introduced into the passageway through the luers.

With sheath connector 56 in face-to-face contact with manifold connector 57, tubular fiber guide 60 is fully inserted, and terminates near the forward end of enlarged passageway portion 116. The larger diameter proximal portion readily allows fluid flow through the annular passage between guide 60 and the passageway wall.

As seen in FIG. 5, zero adjust slide 40 has a generally I-shaped cross-section, with a top portion 132 adapted to be contacted by the user's thumb, an opposed bottom portion 134, and a central upright portion 136. Slide 40 is contained relative to fiber adjust housing 24 by first and second opposed inwardly directed flanges 138 and 140, which together comprise the top of the housing in the area of slide 40. Upright portion 136 is contained in a longitudinal gap between flanges 138 and 140, thus to permit slide 40 to move longitudinally, and vertically, relative to the housing.

A pair of pins, one of which is shown at 142, extend upwardly from the top of zero adjust actuator 80 into a cut-away part of bottom portion 134. A coil spring 144 surrounds pin 142 and is held under compression between bottom portion 134 and the top of actuator 80, to continually urge bottom portion 134 upwardly against flanges 138 and 140. A second coil spring similarly surrounds the other pin. Consequently actuator 80 moves along with slide 40 as the slide travels longitudinally relative to the housing. The actuator is constrained to slide relative to the housing by upper rail 86, including first and second complementary upper rail sections 146 and 148, and by lower rail 94 consisting of first and second lower rail sections 150 and 152.

The upwardly facing surfaces of bottom portion 134 are urged against opposed, downwardly facing surface portions of first and second flanges 138 and 140. By virtue of their shape, these upwardly facing and downwardly facing surface portions comprise first and second complementary locking surfaces which fix slide 40 with respect to the housing in response to the coil spring force. As seen from FIG. 6, slide 40 can be moved downwardly against the spring force in order to separate the locking surfaces from one another, releasing the slide for longitudinal travel.

FIG. 7 shows a series of slide teeth 154 formed in one of the upwardly facing surfaces of bottom portion 134, and a complementary series of housing teeth 156 formed in the downwardly facing surface of second flange 140. Substantially identical rows of teeth are formed on the opposite side of slide 40 and in first flange 138. Each of the teeth has a substantially upright edge and a comparatively gradual edge directed upwardly and to the left as viewed in the figure. Consequently, slide 40 when lockingly engaged with the housing is particularly well constrained against forward movement with respect to the housing, albeit also constrained against rearward travel.

A second pin 156 extends upwardly from actuator 80 rearwardly of first pin 142, and is surrounded by a second coil spring 160 under compression between slide 40 and actuator 80.

A sensor 162 is mounted to actuator 80, and is responsive to its longitudinal position with respect to magnet 100. The magnet and sensor are brought into close proximity with one another whenever leg 98 passes directly beneath actuator 80. Sensor 162 and magnet 100 together form first and second interacting elements of a Hall effect switch that is closed whenever magnet 100 is disposed forwardly of sensor 162, and is open whenever the magnet is rearwardly with respect to the sensor. More particularly, magnet 100 is oriented on leg 98 such that its north pole N lies forwardly of its south pole S. The Hall effect switch closes under the influence of south pole S, while the north pole opens the switch. With the Hall effect switch closed, laser source 26 can be activated by virtue of laser actuator switch 38. When the Hall effect switch is open, however, source 26 cannot be enabled.

The purpose of the Hall effect switch is to prevent transmission of laser energy through optical fiber 22 when its distal end is retracted within catheter 18, to avoid damaging the catheter. Thus, a "zero point" for optical fiber 22, proximal to which the laser cannot be enabled, must be at a point where the distal tip of optical fiber 22 extends to the distal tip of catheter 18, or beyond the catheter distal tip by a preselected amount. While it is possible to select the length of optical fiber 22 and catheter 18 with sufficient care to achieve the desired result, this requires unduly strict manufacturing tolerances.

The zero point is determined when using the catheter and fiber advance assembly as follows. Initially, with catheter manifold 16 separated from fiber advance housing 24, catheter 18 is inserted into the blood vessel requiring treatment. Typically catheter insertion is accomplished with a guide wire inserted into the manifold and catheter by means of a guide wire tube, not shown but similar in construction to tubular fiber guide 60. Once catheter 18 is inserted to the desired location, the guide wire is withdrawn. At this stage, tubular guide 60 is inserted into the catheter manifold, bringing manifold connector 57 and sheath connector 56 in face-to-face relation, and the distal tip of guide 60 near the distal end of the enlarged proximal portion of passageway 114.

Pull ring 54 then is used to draw sheath 52 rearwardly through the housing, in effect to advance housing 24 along the sheath toward the catheter manifold, and simultaneously advance optical fiber 22 into and through catheter 18. By virtue of a lengthwise slit along the sheath, it is separated from the optical fiber, inside the housing, as it is moved rearwardly.

Once sheath 52 has been drawn backwardly a sufficient amount to bring the forward edge of housing 24 over manifold connector 57, connector latch 58 secures the manifold connector to integrally join the manifold and housing, and positioning the distal tip of optical fiber 22 just short of the distal tip of catheter 18.

At this point fiber advance slide 42 should be in its most rearward position relative to the housing. The physician advances fiber 22 using fiber advance slide 42 until the fiber is in a selected orientation relative to catheter 18, as determined by using radiopaque markers or other known techniques. Then, with zero adjust side 40 in its most forward position, the physician presses down on the slide to disengage teeth 154 and 156. Slide 40 then is moved rearwardly until LED 79 is actuated, indicating that laser source 26 can be actuated by actuator switch 38. Thus a zero point is established, and laser 26 can be activated only when fiber advance assembly 90 is moved forwardly beyond this point. Withdrawal of assembly 90 proximally to the zero point automatically disables the laser.

In the course of an angioplasty procedure, the physician may desire to reset the zero point. This is conveniently accomplished by pressing downward on slide 40 and moving the slide to the desired new setting, which ordinarily is forward relative to the original setting. Due to the shape of teeth 154 and 156, forward slide movement does not require their complete disengagement, and thus the teeth provide at least a qualitative tactile sense of the slide's forward movement. At the same time, the teeth are shaped to preclude rearward slide movement without complete disengagement, thus to prevent inadvertent rearward movement which might result in damage to the catheter by premature enabling of laser 26.

Because zero adjust slide 40 positively interlocks with the housing, yet is easily released to slide relative the housing, the physician can set and readjust the zero point with the same hand that holds the fiber advance housing, leaving the other hand free for recording information or performing any other required or desired task. Further, as the slide does not demand undue attention in its adjustment, a greater share of the physician's attention can be directed to the surgical procedure at hand.

What is claimed is:

1. An apparatus for advancing and retracting an energy transmitting fiber within a catheter lumen, and for selectably transmitting energy through the fiber, including:

a fiber advance housing adapted to be held by a hand of an individual during use of the apparatus; a catheter having at least one lumen, and means for securing a proximal end of said catheter integrally with respect to a distal end of said housing; and means for generating energy;

an energy transmitting fiber partially contained in said lumen, running through said housing, and optically connected to said means for generating energy;

a fiber advance assembly fixed to said fiber, means for mounting the fiber advance assembly to reciprocate longitudinally with respect to said housing and to position the fiber advance assembly so as to enable said reciprocation thereof by said hand during said use, for alternatively advancing and retracting said fiber relative to the housing and catheter; a distal portion of said fiber extending beyond the forward end of said catheter when the fiber is fully advanced, said distal portion being entirely contained in said lumen when said fiber is retracted;

an actuator member inside said housing and means for mounting the actuator member to slide longitudinally with respect to said housing over a limited range and independently of said fiber advance assembly; a moving member movable longitudinally relative to the housing and having a portion thereof extended outside of said housing, said moving member being positioned to facilitate said longitudinal movement of the moving member by said hand during said use; and a linking means for joining said moving member and said actuator member whereby the actuator member moves longitudinally with said moving member;

a locking means along the path of travel of said moving member for releasably securing said moving member against said longitudinal movement, said locking means including a first locking surface on said moving member, a complementary second locking surface integral with the housing and facing said first locking surface, and a biasing means for urging said first and second locking surfaces into engagement with each other, said moving member further being positioned to facilitate a transverse movement of the moving member by said hand during said use and against the force of said biasing means, to disengage said locking surfaces and release said moving member for said longitudinal movement thereof; and a switching means in said housing for alternatively permitting and preventing transmission of energy through said fiber from said means for generating energy to said distal portion, said switching means including a first switching element integral with said fiber advance assembly, and a second switching element integral with said actuator means, said switching means being closed to permit said transmission whenever said fiber advance assembly is disposed forwardly of a first select position with respect to said actuator member, and open to prevent said transmission whenever said fiber advance assembly is disposed rearwardly of said first select position, said moving member being further movable by said hand, transversely and against the force of said biasing means, to disengage said locking surfaces and thereby allow said longitudinal movement.

2. The apparatus of claim 1 wherein:
said switching means includes a Hall effect switch comprised of a permanent magnet integral with said fiber advance assembly, and a sensor integral with said actuator member and responsive to the position of the sensor relative to the magnet.

3. The apparatus of claim 2 wherein said means for securing the proximal end of said catheter integrally with respect to said distal end of said housing includes a catheter manifold surrounding said catheter, and means for substantially rigidly securing a proximal end of said manifold to said distal end of said housing.

4. The apparatus of claim 2 wherein:
said means for generating energy is a laser and said transmitting fiber is an optical fiber.

5. The apparatus of claim 2 including:
a first stop means for preventing advancement of said fiber advance assembly beyond a second select position with respect to said actuator member.

6. The apparatus of claim 5 wherein:
said first stop means includes a bar integral with said actuator member, and a leg extended from said fiber advance assembly and positioned to contact said bar when the fiber advance member reaches the second select position.

7. The apparatus of claim 6 including:
a second stop means for preventing advancement of said fiber advance assembly beyond a third, adjustable select position with respect to said actuator member, comprising said leg and an adjustable stop mounted slidably with respect to said actuator member, and an interlocking means for releasably fixing said adjustable stop with respect to said actuator member at a plurality of locations.

8. The apparatus of claim 6 wherein:
said permanent magnet is mounted on said leg.

9. The apparatus of claim 2 wherein:
said actuator member slides on a first rail provided in said housing.

10. The apparatus of claim 9 wherein:
said linking means includes a plurality of pins integral with said actuator member, each pin extended through a cut-away portion in said moving member.

11. The apparatus of claim 10 wherein:
said biasing means includes a coil spring surrounding each pin and under compression between said actuator member and moving member.

12. The apparatus of claim 11 wherein:
said first locking surface includes a plurality of first teeth formed in a first surface of the moving member, and said second locking surface includes a plurality of complementary teeth formed in a second surface in said housing and facing said first surface.

13. The apparatus of claim 12 wherein:
said first teeth and complementary teeth are oriented to particularly prevent forward travel of said moving member relative to said housing when said pluralities of teeth are engaged.

* * * * *